United States Patent [19]

Marciel

[11] Patent Number: Plant 7,689

[45] Date of Patent: Oct. 29, 1991

[54] MINIATURE POT ROSE NAMED DEVIENTE

[75] Inventor: Stanley G. Marciel, Aptos, Calif.

[73] Assignee: DeVor Nurseries, Inc., Watsonville, Calif.

[21] Appl. No.: 529,313

[22] Filed: May 29, 1990

[51] Int. Cl.[5] ..... A01H 5/00

[52] U.S. Cl. ..... Plt./10

[58] Field of Search ..... Plt./10

*Primary Examiner*—James R. Feyrer

*Attorney, Agent, or Firm*—Charles W. Rummler

[57] ABSTRACT

A new and distinct variety of miniature pot rose particularly distinguished by its continuous and profuse production of relatively small blooms of a solid overall Tyrian Purple coloration born on strong, upright stems of a plant having an average height of about 25 cm. at twelve weeks of age in a 4 in. pot. This plant has a vigorous, free branching, upright growth habit with a moderate amount of foliage.

1 Drawing Sheet

BACKGROUND OF THE NEW PLANT

This new pot rose variety originated as a seedling hybrid produced by me at Watsonville, Calif. by my crossing the variety "Orange Sunblaze" (U.S. Plant Pat. No. 4,682) with pollen from an unnamed seedling selected from my collection of greenhouse rose plants maintained in my nursery at Watsonville, Calif. for breeding purposes, the present seedling having been selected by me for propagation because of its profuse production of Tyrian Purple flowers produced on a strong upright bush and propagation was done by me at Watsonville, Calif. by means of cuttings with such satisfactory results that such propagation was carried on through several successive generations which demonstrated conclusively that the novel characteristics of the new plant would hold true from generation to generation and appeared to be firmly fixed.

DESCRIPTION OF THE DRAWING

My new pot rose plant is illustrated by the accompanying full color photographic drawing which shows the plant with blooms in several stages of maturity to demonstrate its form and flower production with color rendition as nearly true to that herein specified as is reasonably possible to obtain by conventional photographic procedures.

DESCRIPTION OF THE NEW VARIETY

The following is a detailed description of my new pot rose plant as observed from greenhouse plants grown at Watsonville, Calif. and with color designations being according to The R.H.S. Colour Chart published by The Royal Horticultural Society of London, England.

THE PLANT

Origin: Seedling.

Parentage;

*Seed parent.*—the variety "Orange Sunblaze" (U.S. Plant Pat. No. 4,682).

*Pollen parent.*—an unnamed, unpatented variety selected from rose plants maintained at Watsonville for breeding purposes.

Classification:

*Botanic.*—Rose Hybrid.

*Commercial.*—Miniature Pot Rose.

Form: An upright free branching bush.

Height: About 25 cm. at twelve weeks of age in a 4 inch pot.

Main stem length: About 152 mm. from the last flower cut.

*Color.*—Yellow-Green 146-A.

Branching character: Free branching.

Growth habit: Vigorous, sturdy and upright.

Foliage:

*Quantity.*—Moderate.

*Number of leaves.*—7 or 8, from the last flower cut.

*Size.*—About 56 mm long in average.

Leaflets:

*Number.*—3 to 7.

*Size.*—About 26 mm. long and 17 mm. wide, in average.

*Shape.*—Ovate with denticulate margin.

*Texture.*—Semi-leathery and smooth.

*Aspect.*—Semi-glossy.

*Color.*—Upper side — Green 137-B. Under side — Yellow Green 147-B.

*Stipules.*—Adnate.

*Rachis.*—About 22 mm. long on a 3 leaf and about 42 mm. long on a 7 part leaf.

*Petioles.*—About 4 mm. long.

Ribs and veins: Slightly depressed on the upper side and rounded on the underside.

Thorns:

*Size.*—About 3 mm.

*Color.*—Red Purple 63-C.

THE BUD

Size: Small, Mini-flora.

*Diameter.*—About 14 mm.

*Length.*—About 15 mm.

Shape: Somewhat urn shaped.

Rate of opening: Slow.

Color of petals:

*When sepals first divide.*—Red Purple 61-B.

*When petals begin to unfurl.*—Red Purple 61-C.

Sepals:

*Number.*—Five.

*Character.*—Branched and curled back when flowers open.

*Color.*—Inside — Yellow Green 147-B. Outside — Yellow Green 146-C.

Calyx:

*Shape.*—Funnel-shaped.
*Size.*—Small, broad and of medium length.
Splitting.—Calyx does not split.
*Aspect.*—Smooth.

Peduncle:
*Length.*—About 40 to 45 mm.
*Character.*—Slight and erect.
*Color.*—Yellow Green 146-A.

THE FLOWER

Blooming habit: Continuous and profusely the year round under greenhouse conditions.

Size of bloom: Small.
*Diameter.*—About 4.6 by 5.1 cm.
*Depth.*—About 19 mm.

Borne: Singly on strong upright stems.

Shape:
*When bloom first opens.*—Cup shaped with center of medium height.
*When bloom matures.*—The shape is somewhat flattened and the petals are nicely imbricated.

Pentalage:
*Number.*—26.
*Number of florets.*—14.
Arrangement.—Imbricated.
*Form.*—Ovate with ruffled margins and acute apex.
*Texture.*—Soft.
*Appearance.*—Velvety.
*Color.*—Outer petals: Upper side body — Tyrian Purple 61-C with base of Chartreuse Yellow 3-C. Reverse side body — Red Purple 63-B. Inside petals: Upper side body — Red Purple 61-C with base of Yellow Green 154-C. Reverse side body — Red Purple 63-B with base of Yellow Green 154-D.
*Petaloids.*—Number: 14. Size: About 12 mm. Color: Red Purple 61-C with base of Yellow 9-D.

Peduncle:
*Length.*—About 40 to 45 mm.
*Color.*—Yellow Green 144-A.
*Character.*—Sturdy for a mini-flora.

Discoloration after full bloom: Very slight.
Persistence: The flowers hang on and dry.
Fragrance: Very slight.
Disease resistance: Moderately resistant to mildew, rust and black spots as observed at Watsonville, Calif.
Lasting quality: Long lasting both on the plant and as a cut flower.

THE REPRODUCTIVE ORGANS

Stamens:
*Number.*—30.
*Arrangement.*—Antrorse.
*Anthers.*—Size: About 3 mm. Color: Yellow Orange 16-B.
*Filaments.*—Length: About 4 mm. Color: Yellow 2-C.
*Pollen.*—Color: Yellow Orange 16-B.

Pistils:
*Number.*—20.
*Styles.*—Length: About 8 mm. Color: Yellow Green 144-D tipped with Red Purple 60-B.
*Stigmas.*—Color: Yellow 11-D.

Character of the ovaries: Slender, long and covered with silvery white hairs.

I claim:

1. The new and distinct variety of pot plant rose, substantially as herein shown and described, particularly characterized by its profuse and continuous production of relatively small Tyrian Purple flowers borne singly on strong stems growing from a plant having an average height of about 25 cm. at the age of about twelve weeks as grown in a 4 in. pot.

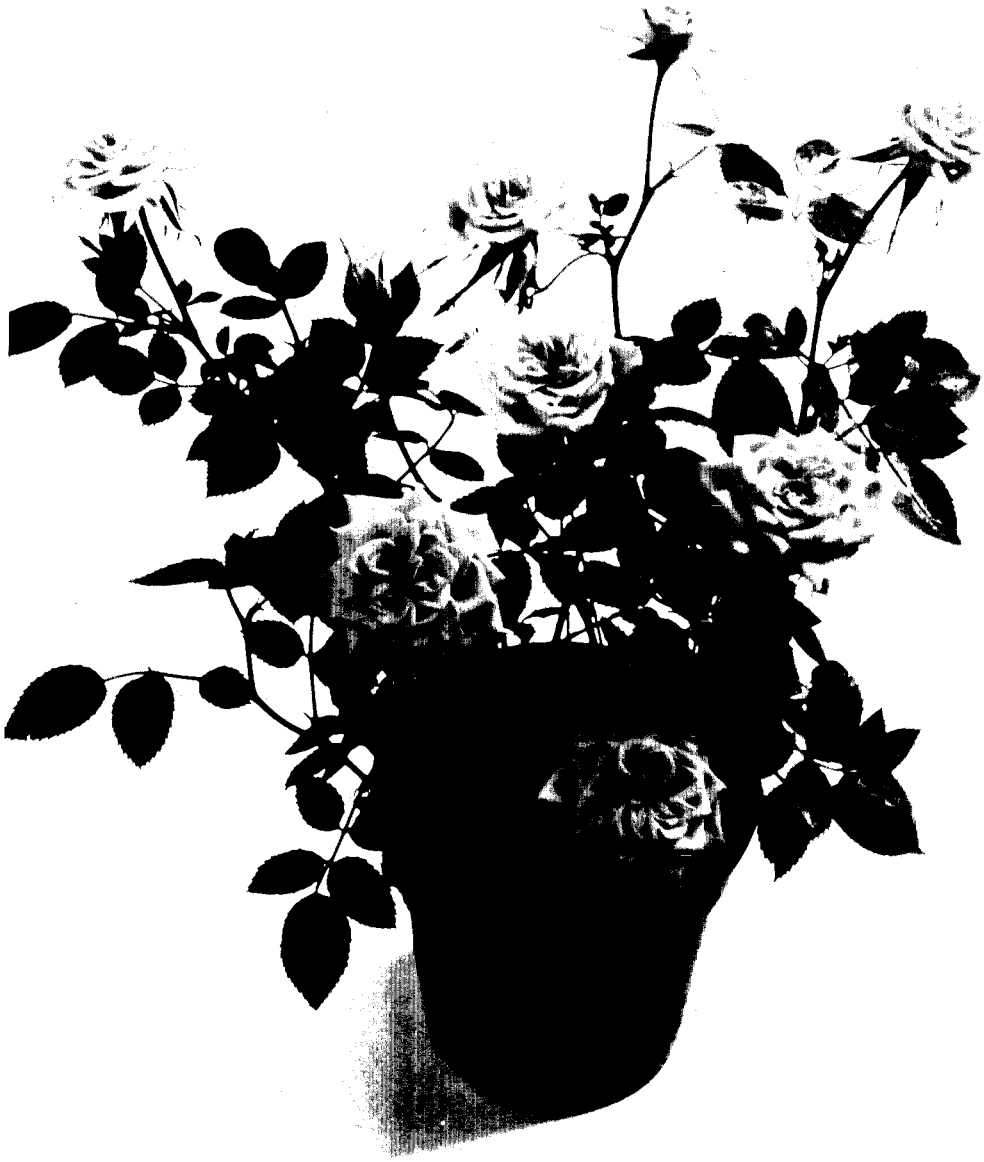

* * * * *